United States Patent [19]
Sanger et al.

[11] Patent Number: 5,952,340
[45] Date of Patent: Sep. 14, 1999

[54] USE OF GRANISETRON FOR THE TREATMENT OF POSTOPERATIVE NAUSEA AND VOMITING

[75] Inventors: Gareth John Sanger, Sawbridgeworth; Philip Timothy Davey, Bishop's Stortford; Christopher Stuart Dott, Reigate, all of United Kingdom

[73] Assignee: SmithKLine Beecham p.l.c., Brentford, United Kingdom

[21] Appl. No.: 08/525,521

[22] PCT Filed: Mar. 15, 1994

[86] PCT No.: PCT/EP94/00820

§ 371 Date: May 23, 1996

§ 102(e) Date: May 23, 1996

[87] PCT Pub. No.: WO94/21257

PCT Pub. Date: Sep. 29, 1994

[30]      Foreign Application Priority Data

Mar. 18, 1993  [GB]  United Kingdom .................. 9305593

[51] Int. Cl.$^6$ ..................................................... A61K 31/44
[52] U.S. Cl. .............................................................. 514/299
[58] Field of Search ............................................... 514/299

[56]         References Cited

U.S. PATENT DOCUMENTS 5,225,407  7/1993  Oakley et al. ........................... 514/215
5,360,820  11/1994  Hagan et al. ............................ 514/559

FOREIGN PATENT DOCUMENTS 0 223 385  5/1987  European Pat. Off. ...... C07D 451/12

OTHER PUBLICATIONS

Carmichael, et al., Anti–Cancer Drugs, vol. 9, 1998, pp. 381–385.
S. Bingham and P.D. King, (1992). In: Bianchi AL, Grelot L, Miller AD, King GL, eds. Mechanisma and control of emesis, Paris: INSERM/John Libbey Eurotext, 223, 249–250.
Buchheit K–H, Games R, Bertholet A, Buscher HH (1989). Gastroenterology, 96, A63.
P.L.R. Andrews, "Physiology of Nausea and Vomiting", *British Journal of Anaesthesia,* 69, No. 7(1), pp. 2–19 (1992).
Bunce et al., "The Role of 5–HT in Postoperative Nausea and Vomiting", *British Journal of Anaesthesia,* 69, No. 7(1), pp. 60–62 (1992).
Russell et al., "5–HT, Antagonists in Postoperative Nausea and Vomiting", *British Journal of Anaesthesia,* 69, No. 7(1), pp. 63–68 (1992).

*Primary Examiner*—Raymond Henley, III
*Attorney, Agent, or Firm*—Wayne J. Dustman; William T. King; Charles M. Kinzig

[57]          ABSTRACT

The present invention is directed to a method for the treatment of post-operative nausea and vomiting wherein granisetron is administered to a patient in need thereof.

8 Claims, No Drawings

USE OF GRANISETRON FOR THE TREATMENT OF POSTOPERATIVE NAUSEA AND VOMITING

This is a 371 of PCT/EP94/00820 filed Mar. 15, 1994.

This invention relates to prevention and treatment of post-operative nausea and vomiting (PONV), and pharmaceutical compositions therefor.

PONV is an important patient problem and one that patients rate as the most distressing aspect of operative procedure, even above pain. Consequently, the need, from the patients' perspective, for an effective anti-emetic in this area is important. As a clinical problem PONV is troublesome and requires staff around to ensure that vomitus is not regurgitated, which can have very serious clinical sequela There are certain operative procedures where it is clinically important that patients do not vomit. For example, in occular surgery where intra-cranialloccular pressure can increase to the extent that stitches are ruptured and the operative procedure is set back in terms of success to a marked degree.

Thus from the point of view of patients and clinicians, the control of PONV is essential.

Financially, the control of PONV is also important. In regions such as the U.S.A., a lot of surgery is done in the day-care setting and the importance of being able to send patients home without an overnight stay is financially attractive. In other countries the popularity of day-care surgery is increasing and it may reach to over 50% in 5–10 years time.

The number of operations done per year in the Western world and Japan is in the order of 65 million. Many anaesthetists currently use prophylactic anti-emetic such as low dose metoclopramide (10 mg) pre- or peri-operatively and many use no prophylactic anti-emetics at all due to poor efficacy of current agents coupled with troublesome side-effects such as dystonic reactions and somnolence. Thus the need for a safer and efficacious antiemetic in PONV is present.

Example 6 of EP-A-200444 (Beecham Group p.l.c.) describes the preparation of the compound, granisetron (or BRL 43694 monohydrochloride) which is available in the United Kingdom as KYTRIL[1] a drug for treating cytotoxic agent induced nausea and vomiting.

[1]registered trade mark of SmithKline Beecham p.l.c.

We have now found that granisetron is of potential use in the prevention and treatment of PONV.

Accordingly, the present invention provides the use of granisetron in the manufacture of a medicament for the treatment (including prophylaxis) of PONV.

The present invention also provides a method of treatment of (including prophylaxis) of PONV in mammals, including man, by administration of granisetron to the mammal in need thereof.

The administration of granisetron may be by way of known methods, such as oral, or parenteral administration.

An amount effective to treat the disorder hereinbefore described depends on the usual factors such as the nature and severity thereof and the weight of the mammal. However, a unit dose will normally contain 0.5 to 10 mg, for example 1 to 3 mg of granistron. A unit dose will normally be administered pre-operatively such as prior to induction of anaesthesia or peri-operatively; and/or post-operatively.

For oral or parenteral administration, it is greatly preferred that granisetron is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing granisetron and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the treatment concerned.

The present invention further provides a pharmaceutical composition for use in the treatment and/(including prophylaxis) of PONV, which comprises granistron and a pharmaceutically acceptable carrier. Such compositions may be prepared in the manner as hereinbefore described.

The following clinical study results illustrate the invention.

Clinical Study Outline

| | |
|---|---|
| Title: | A double blind parallel group placebo controlled dose ranging study of intravenous granisetron in the prevention of post-operative nausea and vomiting in patients undergoing open surgery. |
| Indication: | For the prevention of post-operative nausea and vomiting. |
| Objective: | To determine the optimum dose of intravenous granisetron to prevent post-operative nausea and vomiting. |
| Study Population: | 480 evaluable patients (120 per group) who are scheduled to undergo general anaesthesia for elective open surgery for gynaecological procedures or cholecystectomy. |
| Efficacy Parameters: | Primary efficacy assessment will be the no vomiting rate, over 0–6 hours and 0–24 hours. Secondary efficacy assessments will include analysis of time to:<br>i) total control rate (no nausea, no vomit/retching, no rescue antiemetic and not withdrawn)<br>ii) less than total control.<br>iii) forst episode of vomiting.<br>iv) first episode of nausea.<br>v) nausea and vomiting rate over day 0–6. |
| Safety Parameters: | Safety will be assessed by recording:<br>a Vital signs<br>b Laboratory variables<br>c Adverse experiences<br>d Concurrent medication |
| Dosing Schedule: | Patients will be randomised to receive placebo, 0.1 mg, 1.0 mg or 3.0 mg IV granisetron given as a 30 second injection at induction of anaesthesia. |
| Efficacy Assessments: | On Day 0 assessments will be made at 1 hour, 2 hours, 6 hours, and 24 hours of nausea (none, mild, moderate or severe) and vomiting (none, 1, 2, 3, 4, or >4 episodes) in the CRF. On Days 1–6 daily assessments of nausea and vomiting will be made on a diary card. |

RESULTS

DOSE RANGING STUDY (PONV) PLACEBO vs 0.1MG vs 1.0MG vs 3.0MG I.V.

| | NO VOMITING | | | | | | | |
|---|---|---|---|---|---|---|---|---|
| | TREATMENT GROUP | | | | | | | |
| | PLACEBO | | 0.1 MG | | 1.0 MG | | 3.0 MG | |
| | n | % | n | % | n | % | n | % |
| Vomiting Status 0–6 hrs | | | | | | | | |
| Vomiting | 67 | 50.38 | 55 | 41.67 | 29 | 21.64 | 30 | 23.44 |
| No Vomiting | 66 | 49.62 | 77 | 58.33 | 105 | 78.36 | 98 | 76.56 |
| Vomiting Status 0–24 hrs | | | | | | | | |
| Vomiting | 88 | 66.17 | 73 | 55.30 | 49 | 36.57 | 49 | 38.28 |
| No Vomiting | 45 | 33.83 | 59 | 44.70 | 85 | 63.43 | 79 | 61.72 |

Confidence Intervals

Approximate pairwise confidence intervals for the difference in the proportion of vomiting responders, based on a quadratic approximation to the log-likelihood, have been calculated for each treatment group, using the Bonferroni correction (to maintain the two-tailed significance level of 5%)

| Pairwise Comparison | Confidence Interval | p value | *sig |
|---|---|---|---|
| 0–6 hours | | | |
| BRL 0.1 MG IV vs PLACEBO IV | [−4.95%, 22.37%] | p = 0.155 | NS |
| BRL 1.0 MG IV vs PLACEBO IV | [16.17%, 41.29%] | p < 0.001 | SIG |
| BRL 3.0 MG IV vs PLACEBO IV | [14.11%, 39.77%] | p < 0.001 | SIG |
| 0–24 hours | | | |
| BRL 0.1 MG IV vs PLACEBO IV | [−2.50%, 24.22%] | p = 0.07 | NS |
| BRL 1.0 MG IV vs PLACEBO IV | [16.51%, 42.69%] | p < 0.001 | SIG |
| BRL 3.0 MG IV vs PLACEBO IV | [14.57%, 41.19%] | p < 0.001 | SIG |

PLACEBO vs 0.1 MG vs 1.0 MG vs 3.0 MG I.V.

| | NO NAUSEA | | | | | | | |
|---|---|---|---|---|---|---|---|---|
| | TREATMENT GROUP | | | | | | | |
| | PLACEBO | | 0.1 MG | | 1.0 MG | | 3.0 MG | |
| | n | % | n | % | n | % | n | % |
| Nausea Status 0–6 hrs | | | | | | | | |
| Nausea | 87 | 65.41 | 81 | 61.36 | 49 | 36.57 | 55 | 42.97 |
| No Nausea | 46 | 34.59 | 51 | 38.64 | 85 | 63.43 | 73 | 57.03 |
| Nausea Status 0–24 hrs | | | | | | | | |
| Nausea | 104 | 78.20 | 95 | 71.97 | 67 | 50.00 | 74 | 57.81 |
| No Nausea | 29 | 21.80 | 37 | 28.03 | 67 | 50.00 | 54 | 42.19 |

*Significance using Modified Bonferroni Correction.

Confidence Intervals

Approximate pairwise confidence intervals for the difference in the proportion of vomiting responders, based on a quadratic approximation to the log-likelihood, have been calculated for each treatment group, using the Bonferroni correction (to maintain the two-tailed significance level of 5%)

| Pairwise Comparison | Confidence Interval | p value | *sig |
|---|---|---|---|
| 0–6 hours | | | |
| BRL 0.1 MG IV vs PLACEBO IV | [−9.20%, 17.30%] | p = 0.494 | NS |
| BRL 1.0 MG IV vs PLACEBO IV | [15.73%, 41.97%] | p < 0.001 | SIG |
| BRL 3.0 MG IV vs PLACEBO IV | [8.97%, 35.91%] | p < 0.001 | SIG |
| 0–24 hours | | | |
| BRL 0.1 MG IV vs PLACEBO IV | [−5.64%, 18.10%] | p = 0.241 | NS |
| BRL 1.0 MG IV vs PLACEBO IV | [15.63%, 40.77%] | p < 0.001 | SIG |
| BRL 3.0 MG IV vs PLACEBO IV | [7.73%, 33.03%] | p < 0.001 | SIG |

-continued

PLACEBO vs 0.1 MG vs 1.0 MG vs 3.0 MG I.V.
TOTAL CONTROL

| | TREATMENT GROUP | | | | | | | |
|---|---|---|---|---|---|---|---|---|
| | PLACEBO | | 0.1 MG | | 1.0 MG | | 3.0 MG | |
| | n | % | n | % | n | % | n | % |
| Total Control Status 0–6 hrs | | | | | | | | |
| Less than Total Control | 91 | 68.42 | 83 | 62.88 | 49 | 36.57 | 58 | 45.31 |
| Total Control | 42 | 31.58 | 49 | 37.12 | 85 | 63.43 | 70 | 54.69 |
| Total Control Status 0–24 hrs | | | | | | | | |
| Less than Total Control | 109 | 81.95 | 97 | 73.48 | 68 | 50.75 | 74 | 57.81 |
| Total Control | 24 | 18.05 | 35 | 26.52 | 66 | 49.25 | 54 | 42.19 |

*Significance using Modified Bonferroni Correction.

Confidence Intervals

Approximate pairwise confidence intervals for the difference in the proportion of vomiting responders, based on a quadratic approximation to the log-likelihood, have been calculated for each treatment group, using the Bonferroni correction (to maintain the two-tailed significance level of 5%)

| Pairwise Comparison | Confidence Interval | p value | *sig |
|---|---|---|---|
| 0–6 hours | | | |
| BRL 0.1 MG IV vs PLACEBO IV | [−7.51%, 18.59%] | p = 0.342 | NS |
| BRL 1.0 MG IV vs PLACEBO IV | [18.87%, 44.83%] | p < 0.001 | SIG |
| BRL 3.0 MG IV vs PLACEBO IV | [9.74%, 36.48%] | p < 0.001 | SIG |
| 0–24 hours | | | |
| BRL 0.1 MG IV vs PLACEBO IV | [−2.93%, 19.87%] | p = 0.097 | NS |
| BRL 1.0 MG IV vs PLACEBO IV | [18.99%, 43.43%] | p < 0.001 | SIG |
| BRL 3.0 MG IV vs PLACEBO IV | [11.84%, 36.44%] | p < 0.001 | SIG |

*Significance using Modified Bonferroni Correction.

Time to first Vomiting (24 hour period)

Forty-five patients (33.83%) in the Placebo group, 59 (44.70%) in the 0.1 MG group, 85 (63.43%) in the 1.0 MG group and 79 (61.72%) in the 3.0 MG group did not experience any vomiting over the 24 hour period. There was evidence to suggest a difference in the survival distributions to times of first vomiting ($\chi^2=36.1544$, df=3, p<0.001).

Using the Modified Bonferroni correction for the three pairwise comparisons, there was insufficient evidence to suggest a significant difference between placebo and 0.1 MG ($\chi^2=3.0313$, df=1, p=0.082), but there was a significant difference between placebo and 1.0 MG ($\chi^2=25.9298$, df=1, p<0.001), and between placebo and 3.0 MG ($\chi^2=21.9885$, df=1, p<0.001) in the survival distributions of times to first vomiting.

Time to first Nausea (24 hour period)

Twenty-nine patients (21.80%) in the placebo group, 37 patients (28.03%) in the 0.1 MG group, 67 patients (50.00%) in the 1.0 MG group and 54 patients (42.19%) in the 3.0 MG group did not experience any nausea over the 24 hour period. There was evidence to suggest a difference in the survival distributions of times to first nausea ($\chi^2=30.1666$, df=3, p<0.001).

Using the Modified Bonferroni correction for the three pairwise comparisons, there was insufficient evidence to suggest a significant difference between placebo and 0.1 MG ($\chi^2=1.5899$, df=1, p=0.2073),but there was a significant difference between placebo and 1.0 MG ($\chi^2=23.3685$, df=1, p<0.001) and between placebo and 3.0 MG ($\chi^2=13.9814$, df=1, p<0.001), in the survival distributions of times to first nausea episode.

Time to less than Total Control (24 hour period)

Twenty-four patients (18.05%) in the placebo group, 35 patients (26.52%) in the 0.1 MG group, 66 patients (49.25%) in the 1.0 MG group and 54 patients (42.19%) in the 3.0 MG group maintained total control over the whole 24 hour period. There was evidence to suggest a significant difference in the survival distributions of times to less than total control ($\chi^2=37.0051$, df=3, p<0.001).

Using the Modified Bonferroni correction for the three pairwise comparisons there was insufficient evidence to suggest a difference between the placebo and 0.1 MG group ($\chi^2=2.7620$, df=1, p=0.097), but there was a significant difference between placebo and 1.0 MG ($\chi^2=29.5533$, df=1, p<0.001) and between placebo and 3.0 MG ($\chi^2=18.2882$, df=1, p<0.001), in the survival distributions of times to less than total control.

Time to first use of Rescue (24 hour period)

Eighty patients (60.15%) in the placebo group, 89 patients (67.42%) in the 0.1 MG group, 101 patients (75.37%) in the 1.0 MG group and 99 patients (77.34%) in the 3.0 MG group did not require any rescue medication over the 24 hour study period. There was evidence to suggest a significant difference in the survival distributions of times to use of anti-emetic therapy ($\chi^2=12.1904$, df=3, p=0.007).

Using the Modified Bonferroni correction for the three pairwise comparisons there was insufficient evidence to suggest a significant difference between placebo and 0.1 MG ($\chi^2=1.4836$, df=1, p=0.223), but there was a significant difference between placebo and 1.0 MG ($\chi^2=7.3467$, df=1, p=0.007) and between placebo and 3.0 MG ($\chi^2=9.0949$, df=1, p=0.003), in the survival distributions of times to first use of rescue therapy.

We claim:

1. A method of treatment of post-operative nausea and vomiting (PONV) in mammals, including man, by administration of granisetron to the mammal in need thereof.

2. A method according to claim 1 wherein the granisetron is adapted for intravenous administration.

3. A method according to claim 1 wherein granisetron is administered in a 1 mg to 3 mg unit dose.

4. A method according to claim 1 wherein granisetron is administered pre-operatively, peri-operatively; or post-operatively.

5. A method according to claim 4 wherein granisetron is administered pre-operatively.

6. The method of claim 1 wherein from about 1 mg to about 3 mg of granisetron is administered pre-operatively.

7. The method of claim 1 wherein from about 1 mg to about 3 mg of granisetron is administered peri-operatively.

8. The method of claim 1 wherein from about 1 mg to about 3 mg of granisetron is administered post-operatively.

* * * * *